United States Patent [19]

Klaenhammer et al.

[11] Patent Number: 4,883,756

[45] Date of Patent: Nov. 28, 1989

[54] PTN1060, A CONJUGAL PLASMID AND DERIVATIVES THEREOF THAT CONFER PHAGE RESISTANCE TO GROUP N STREPTOCOCCI

[75] Inventors: Todd R. Klaenhammer; Rosemary B. Sanozky-Dawes, both of Raleigh, N.C.

[73] Assignee: North Carolina State University, Raleigh, N.C.

[21] Appl. No.: 942,524

[22] Filed: Dec. 16, 1986

[51] Int. Cl.$^4$ .................. C12N 1/20; C12N 15/00; C12R 1/46; A23C 9/123

[52] U.S. Cl. .................. 435/252.3; 435/252.4; 435/320; 435/885; 426/43; 426/61

[58] Field of Search .................. 435/320, 235, 172.3, 435/885, 253, 252.3, 252.4; 935/55, 72; 426/34, 43, 61

[56] References Cited

U.S. PATENT DOCUMENTS 4,530,904  7/1985  Heishberger et al. ............ 435/172.3

OTHER PUBLICATIONS

McKay, L. L. et al; Conjugative 40-Megadalton Plasmid in S. lactis subsp diacetylactic, DRC3, is Associated with Resistance to NISIN and Bacteriophage Appl. Enviro. Microbiol, 47 (1) pp. 68-74 (1984).

Klaenhammer, T. R.; Interactions of Bacteriophages with Lactic Streptococci; Adv Appl Microbiol, 30, pp. 1-29 (1984).

Steenson, L. R. et al; S. Cremoris M12R Transconjugates Carrying the Conjugal plasmid pTR2030 are Insensitive to Attack by Lytic Bacteriophage; Appl. Enviro Microbiol 50 (4) 85-1-852 (1985).

Klaenhammer, T. R. et al; Conjugal Transfer from S. Lactics Mez of Plasmids Encoding Phage Resistance, Nizon Resistance and Lactose Fermenting Ability; J. Gen. Microbiol., 131, pp. 1531-1541 (1985).

Sanders, M. E. et al., *Appl. Environ. Microbiol.* 40, 500 (1980).

Sanders, M. E. et al., *Appl. Environ. Microbiol.* 42, 944 (1981).

Sanders, M. E. et al., *Appl. Environ. Microbiol.* 46, 1125 (1983).

Chopin, A. et al., *Plasmid* 11, 260 (1984).

Klaenhammer, T. R., *Adv. Appl. Microbiol.* 30, 1 (1984).

McKay, L. L. et al., *Appl. Environ. Microbiol.* 47, 68 (1984).

Sanders, M. E. et al., *Appl. Environ. Microbiol.* 47, 979 (1984).

Gonzalez, C. F. et al., *Appl. Environ. Microbiol.* 49, 627 (1985).

Klaenhammer, T. R. et al., *J. Gen. Microbiol.* 131, 1531 (1985).

Jarvis, A. W., et al., *Appl. Environ. Microbiol.* 51, 1272 (1986).

Steenson, L. R. et al., *Appl. Environ. Microbiol.* 50, 851 (1985).

Sing, W. D. et al., *Appl. Environ. Microbiol.* 51, 1264 (1986).

*Primary Examiner*—Elizabeth C. Weimar
*Attorney, Agent, or Firm*—Bell, Seltzer, Park & Gibson

[57] ABSTRACT

The present invention relates to the plasmid pTN1060 and derivatives thereof which confer phage restriction and modification activity to group N streptococci. The invention further relates to microorganisms containing pTN1060 or a derivative thereof and to starter cultures containing the microorganisms.

12 Claims, 1 Drawing Sheet

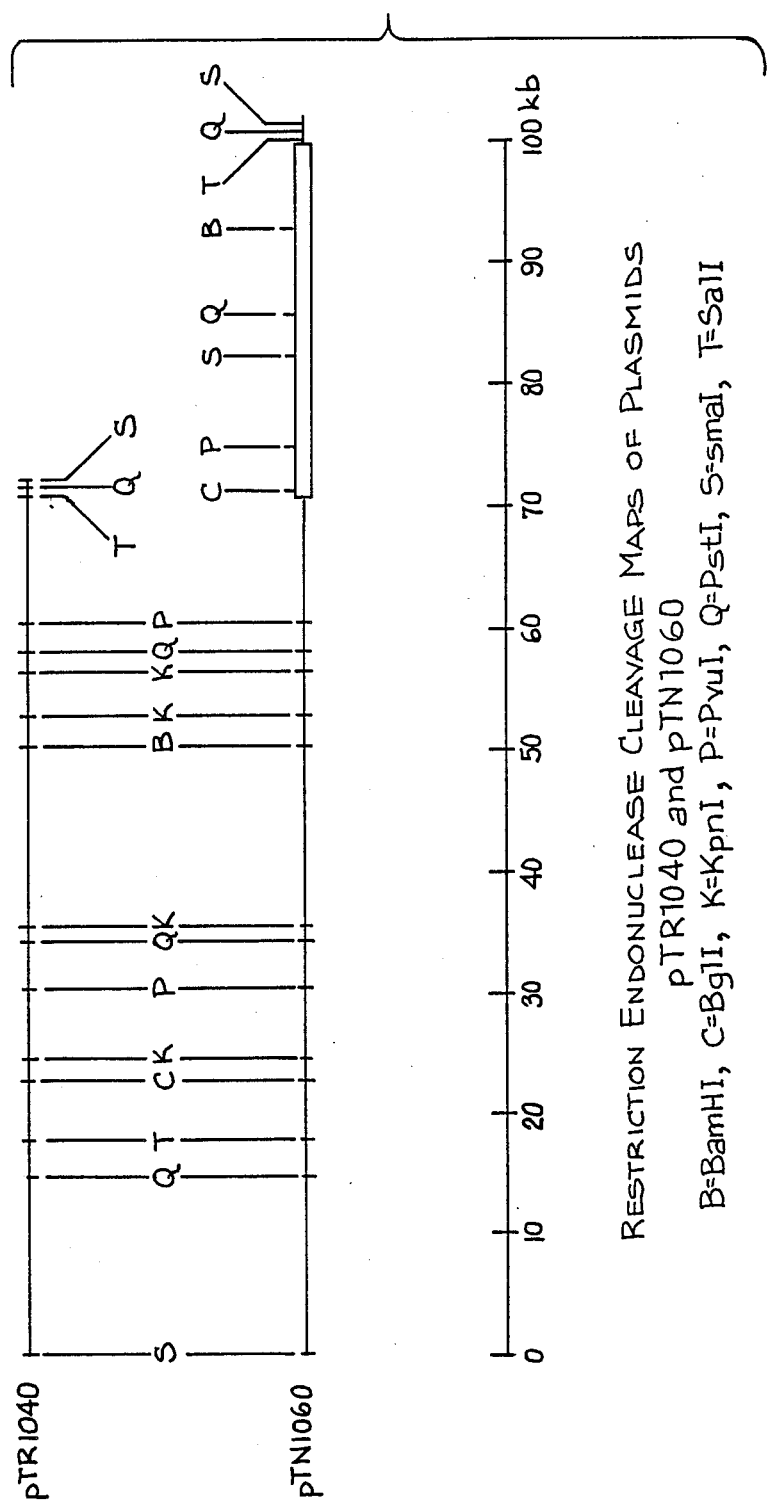

PTN1060, A CONJUGAL PLASMID AND DERIVATIVES THEREOF THAT CONFER PHAGE RESISTANCE TO GROUP N STREPTOCOCCI

FIELD OF THE INVENTION

The present invention relates to the plasmid pTN1060 and to derivatives thereof. More specifically, the present invention relates to the plasmid pTN1060 which carries a genetic determinant for phage restriction and modification activity in group N streptococci and to derivatives of this plasmid which also carry this genetic determinant.

BACKGROUND OF THE INVENTION

Production of cheese and cultured dairy products has long relied on the fermentation of milk by group N streptococci. Members of this group, composed of *Streptococcus lactis, S. cremoris,* and *S. lactis* subsp. *diacetylactis,* are directly responsible for the acid development, flavor production, and often coagulum characteristics in mesophilic dairy fermentations. Because efficient milk fermentations are dependent on the growth and activity of the lactic streptococci, great care is exercised to prepare starter cultures that are highly active and uncontaminated with undesirable microorganisms or bacteriophages. However, the fermentation process itself is nonaseptic, occurring in open vats with a nonsterile medium, pasteurized milk. It is therefore highly susceptible to contamination with bacteriophages. For the majority of strains of lactic streptococci employed in commercial dairy fermentations, lytic bacteriophages capable of halting growth and acid production can appear within one to two days after introducing the culture into the cheese plant. Although bacteriophage contamination of numerous industrial fermentations has been observed, the destructive role of bacteriophages in milk fermentations is without parallel in other fermentation processes.

Historically, milk fermentations relied on starter cultures composed of undefined mixtures of lactic streptococci propagated without knowledge of, or protection from, bacteriophages. Natural phage contamination in these cultures established an equilibrium of evolving bacteriophages and phage-resistant variants. These cultures were highly variable in day-to-day levels of acid production, but remained moderately active and could be used continuously in small fermentation factories. Over the past 20 years, starter culture failures due to bacteriophage infection have become prevalent throughout the dairy industry. Increasing demand for cultured milk products in recent years has necessitated increases in both production capacity and process efficiency such that larger volumes of milk are processed, cheese vats are filled repeatedly within a single day, and total processing time is shortened. This modernization of the industry concurrently increased the probability of phage contamination and further dictated the use of defined mixtures of lactic streptococci capable of uniform and rapid rates of acid production. With the selection of highly fermentative lactic streptococci and their propagation under aseptic conditions (in the absence of bacteriophages), the majority of cultures now used by the industry have become highly susceptible to bacteriophage attack upon introduction into the cheese factory.

To cope with bacteriophage problems a number of successful methods have been developed to minimize phage action during commercial milk fermentations. Through the use of concentrated cultures, aseptic bulk starter vessels and phage-inhibitory media (see, for example, U.S. Pat. No. 4,282,255), the starter culture can be protected from bacteriophage infection prior to vat inoculation. However, phage contamination cannot be prevented following entrance into the fermentation vat. Therefore, emphasis for protection of the culture shifts to minimizing prolific phage-host interactions through rotation of phage-unrelated strains or use of phage-resistant mutants in multiple-strain starters. Although, in theory, strain rotation should minimize developing phage populations within the plant, in practice it has proved difficult to identify strains that demonstrate completely different patterns of phage sensitivity. Estimates of the total number of different, phage-unrelated lactic streptococci approximate 25 strains worldwide. Considering the small number of phage-unrelated strains available, the choice of strains for incorporation into rotation programs is severely limited. Similarly, few phage-unrelated strains are available for construction of multiple-strain starters containing composites of four to six strains.

A decade ago, Sandine, W. E., et al., *J. Milk Food Technol.* 35, 176 (1972) emphasized the need to isolate new strains of lactic streptococci for use in the dairy industry. Foremost among the criteria for selection of these strains was resistance to existing bacteriophages. It is now recognized that some strains of lactic streptococci are not attacked by any phage when challenged with large collections of laboratory phage banks, or when used on a continuous, long-term basis in commercial fermentations. These reports demonstrate the existence of lactic streptococci that are not sensitive to bacteriophage attack, in spite of devastating phage pressure such as that which routinely occurs within the factory environment. However, to date, only a limited number of phage-insensitive strains have been identified and studied for mechanism of phage resistance.

*Streptococcus lactis* ME2 has been shown to exhibit at least three independent phage defense mechanisms that functioned cooperatively to confer an apparent phage-insensitive state. Sanders, M. E. and T. R. Klaenhammer, *Appl Environ. Microbiol.* 46, 1125 (1983); Sanders, M. E. and T. R. Klaenhammer, *Appl. Environ. Microbiol.,* 47, 979 (1984). Inhibition of bacteriophage by ME2 was initially characterized to include the following reactions: (i) phage adsorption was retarded in the presence of a 30 Md plasmid, pME0030; (ii) restriction and modification activities were exhibited; and (iii) a heat-sensitive inhibition of phage burst size occurred for modified phage propagated on the adsorption variant, *S. lactis* N1. Subsequent characterization of *S. lactis* ME2 exconjugants identified a 30 Md conjugative plasmid (pTR2030) that imposed either a heat-sensitive reduction in burst size of prolate phages without altering the plaquing efficiency, Klaenhammer, T. R. and R. B. Sanozky, *J. Gen. Microbiol.* 131, 1531 (1985), or a complete elimination of the plaquing ability of small isometric phages without affecting the level of phage adsorption, Jarvis, A. W. and T. R. Klaenhammer, *Appl. Environ. Microbiol.* 51, 1272 (1986); Steenson, L. R. and T. R. Klaenhammer, *Appl. Environ. Microbiol.* 50, 851 (1985). Introduction of pTR2030 to phage-sensitive lactic streptococci provided effective protection against small isometric phages in general, without altering the fermentative ability of the strains constructed, Sing, W.

D. and T. R. Klaenhammer, *Appl. Environ. Microbiol.* 51, 1264 (1986). Host dependent phage replication could not be demonstrated on pTR2030 transconjugants, providing evidence that the mechanism of pTR2030-induced resistance did not involve phage restriction and modification activities. Klaenhammer and Sanozky, supra.

Plasmids encoding mechanisms for phage restriction and modification activity appear widely distributed throughout group N streptococci and can be effective in inhibiting heterologous phage attack, depending on the level of phage restriction imposed. Boussemaer, J. P. et al., *J. Dairy Res.* 47, 401 (1980); Klaenhammer, T. R., *Adv. Appl. Microbiol.* 30, 1 (1984); Pearce, L. E., *N.Z.J. Dairy Sci. Technol.* 13, 166 (1978). Host-dependent phage replication has been correlated to the presence of a 10 Md plasmid in *S. cremoris* KH. Sanders, M. E. and T. R. Klaenhammer, *Appl. Environ. Microbiol.* 42, 944 (1981).

Chopin, A. et al., *Plasmid* 11, 260 (1984) report the conjugal transfer of 28 and 31 kilobase plasmids responsible for restriction and modification of phage in lactic streptococci, and suggested that interactions between these and other plasmids affected the level of phage restriction. The plasmids were found in *Streptococcus lactis* strain IL 594. It was not indicated whether or not the plasmids carried their own transfer determinants.

Hershberger, C. L., U.S. Pat. No. 4,530,904, discloses a method for protecting bacteria in general from different types of bacteriophage. The method involves transforming a bacterium with a recombinant DNA cloning vector. The recombinant vector comprises a replicon that is functional in the bacterium, a gene that expresses a functional polypeptide (i.e., human growth hormone) in the bacterium, and a DNA segment which confers restriction and modification activity to the bacterium. The transformed bacterium is then cultured under large-scale fermentation conditions. This method is particularly adapted to fermentation procedures for the production of polypeptide products like growth hormone.

The identification or creation of plasmids encoding for restriction and modification activity in group N streptococci is necessary in order to genetically engineer strains that meet industrial criteria for fermentative capabilities and long-term phage resistance. The present invention provides for a plasmid which confers phage restriction and modification activity to group N streptococci. Group N streptococci containing the plasmid or a derivative thereof are useful for formulating starter cultures which can be used for the production of cheese and cultured dairy products.

SUMMARY OF THE INVENTION

The present invention comprises a plasmid or a derivative thereof which confers bacteriophage restriction and modification activity to group N streptococci. The present invention also comprises group N streptococci containing the plasmid or derivative. The present invention further comprises starter cultures containing such streptococci.

More specifically, the present invention comprises the plasmid pTN1060 and derivatives thereof which confer phage restriction and modification activity to group N streptococci. pTN1060 carries a genetic determinant for phage restriction and modification activity. Derivatives of pTN1060 are considered herein to mean any plasmid capable of replication, transcription and translation in group N streptococci which carries the genetic determinants for phage restriction and modification. The invention further comprises group N streptococci which contain plasmid pTN1060 or derivatives thereof and starter cultures for fermenting milk or fermenting food containing these group N streptococci. Preferred streptococci include strains of *S. lactis, S. lactis* subsp. *diacetylactis,* and *S. cremoris.*

DETAILED DESCRIPTION OF THE INVENTION

The present invention is directed to the plasmid pTN1060 and its derivatives which are useful for conferring phage restriction and modification activity to group N streptococci. The latter are useful for formulating starter cultures for use in the production of cheese and cultured dairy products. pTN1060 and its derivatives could also be useful for conferring phage resistance to other gram-positive lactic acid bacteria used in dairy and food fermentation. pTN1060 carries a genetic determinant which confers phage restriction and modification activity. The plasmid further carries genetic determinants for conjugal transfer. This genetic determinant promotes its own transfer as well as the transfer of other non-conjugative plasmids. The plasmid still further carries genetic determinants for lactose fermentation and nisin resistance. A derivative of pTN1060 is used herein to refer to any plasmid capable of replication, transcription and translation in group N streptococci or other gram-positive lactic acid bacteria which is either (a) pTN1060 with inserted DNA sequences, or (b) pTN1060 with DNA sequences deleted, or (c) pTN1060 with inserted and deleted DNA sequences, or (d) a plasmid with a significant portion of at least one of the pTN1060 genetic determinants for phage restriction and modification activity inserted therein.

Plasmid pTN1060 was formed in vivo by a recombinational event between pTR1040 encoding Lac+ and Nis$^r$, and a 20 Md DNA fragment encoding conjugal transfer ability and phage restriction and modification activity. Although the Lac+ Nis$^r$ plasmid pTR1040 can be mobilized from *S. lactis* ME2 by the conjugative plasmid pTR2030, pTR1040 alone cannot promote its own genetic transfer. Similarly, the presence of pTR1040 alone has not been responsible for any level of bacteriophage resistance exhibited in *S. lactis* L2FA, *S. lactis* LM0230, *S. cremoris* M43a, and *S. cremoris* KH where this plasmid has been introduced and used previously as a marker to follow conjugative events. pTN1060 exhibited conjugal transfer of Lac+ at high frequency, imposed R/M+ activity, and was successfully introduced into four different host backgrounds at frequencies ranging from $7 \times 10^{-6}$ to six recombinants per donor cell. These observations indicate that acquisition of the 20 Md sequence by pTR1040 was responsible for expression of R/M+ and Tra+ phenotypes by pTN1060.

Restriction endonuclease cleavage maps of plasmids pTR1040 and pTN1060 are shown in the accompanying Figure. The scale in the Figure represents length in kilobases.

Plasmid pTN1060 exhibits phenotypes of Tra+, Lac+, Nis$^r$, R/M+, and Clu−. These phenotypes are described as follows:

Tra+: pTN1060 is a conjugative plasmid that promotes its own transfer and the transfer of other non-conjugative plasmids. Consequently, pTN1060 can be used for mobilizing other plasmids in group N streptococci and possibly other gram-positive bacteria (i.e., *S. faecalis,* lactobacilli).

Lac+, Nis' group N streptococci harboring pTN1060 ferment lactose and are resistant to the antimicrobial protein nisin. These two genetic markers are useful for identifying conjugal recipients of pTN1060.

R/M+: pTN1060 transconjugants exhibit restriction and modification activity affecting prolate, small isometric and large isometric phages. The level of phage restriction varies proportionately with the respective genome size of the phage. The availability of this conjugative plasmid encoding R/M+ activity affords expanded opportunities for the construction of phage-resistant starter cultures via genetic strategies.

Clu−: pTN1060 exhibits high-frequency conjugal transfer in agar-surface matings. pTN1060 does not induce the "clumping phenotype" (Clu+) in liquid media that has been observed previously for high-frequency conjugal plasmids of group N. streptococci (Walsh, P. M. et al., *J. Bacteriol.* 146, 937 (1983); Anderson, D. G. et al., *J. Bacteriol.* 158, 954 (1984); Gasson, M. J. et al., *J. Bacteriol.* 143, 1260 (1980)). This Clu− phenotype is most desirable because the presence of this conjugal plasmid will not impose cell aggregation in transconjugants carrying pTN1060. Aggregating cultures are unsuitable for most applications in dairy and food fermentations.

Derivatives of pTN1060 include the following plasmids: (a) plasmid pTN1060 into which DNA sequences have been inserted; (b) plasmid pTN1060 from which DNA sequences have been deleted; (c) plasmid pTN1060 into which DNA sequences have been inserted and from which DNA sequences have been deleted; and (d) any plasmid into which the pTN1060 genetic determinants for phage restriction and modification activity has been inserted. Additionally, a derivative of pTN1060 can include any plasmid into which any DNA sequence of pTN1060 has been inserted. It is preferred that each of these derivatives contain the pTN1060 genetic determinant for phage restriction and modification activity. It is further preferred that each of these derivatives contain the pTN1060 genetic determinants for conjugal transfer. Each of these derivatives may contain the pTN1060 genetic determinants for lactose fermentation, and, optionally, nisin resistance, as markers for transfer experiments.

The derivatives of pTN1060 can be prepared by using techniques well known in the art. Thus, insertions and/or deletions to pTN1060 can be performed using standard techniques. Many standard techniques have been described by Maniatis, T. et al., *Molecular Cloning: A Laboratory Manual,* Cold Spring Harbor Laboratory (1982). Similarly, the pTN1060 genetic determinant for phage restriction and modification activity (or any other pTN1060 DNA sequence) can be inserted into any plasmid using conventional techniques such as those described by Maniatis, T. et al., supra. A genetic determinant can be first isolated from pTN1060 and then inserted into a second plasmid. The second plasmid can be further tailored if necessary. The pTN1060 genetic determinant for phage restriction and modification activity can be isolated as follows. Restriction fragments of pTN1060 are isolated and inserted into an appropriate plasmid vehicle for transformation into a suitable cloning host (for example *S. lactis, E. coli,* and *B. subtilis*). The recombinant plasmid is then introduced into *lacti streptococci* and then the transformed bacteria analyzed for phage resistance phenotypes. Resistant colonies contain a plasmid carrying the pTN1060 genetic determinant for phage restriction and modification activity. The restriction fragment with this determinant can be further manipulated as may be required, by using conventional techniques.

Suitable hosts for the plasmid pTN1060 or its derivatives are any microorganism in which pTN1060 or its derivatives are capable of replication. Preferred hosts are group N streptococci which include strains which are used in the production of cheese and cultured dairy products. Examples of these hosts are strains of *S. lacti, S. lactis* subsp. *diacetylactis,* and *S. cremoris.* Additional hosts include gram-positive lactic acid bacteria which are used in dairy and food fermentations. Examples of these hosts include strains of *Lactobacillus, Pediococcus* and *Leuconostoc.* Plasmid pTN1060 or its derivatives can be introduced into any suitable host using standard techniques. Such techniques can include conjugal transfer as well as transformation.

Microorganisms containing pTN1060 or its derivatives preferably exhibit a phage restriction and modification phenotype. As a result of this property, the microorganisms with pTN1060 or its derivatives are extremely useful in the production of cheese and cultured dairy products as well as other food and dairy fermentations. The microorganisms are capable of more efficient fermentation since they are less sensitive to phages which are present or likely to appear in the fermentation vessel. Microorganisms containing pTN1060 or its derivatives are useful in formulation of starter cultures for the production of cheese and cultured dairy products. The preparation and use of starter cultures are well known in the art. Consequently, starter cultures can be formulated by using a microorganism containing pTN1060 or its derivatives in place of, or in conjunction with, microorganisms currently employed. For example, a strain of *S. cremoris* carrying pTN1060 can be used in preparing a starter culture in place of the original strain of *S. cremoris* lacking pTN1060.

The present invention will be further described by reference to the following non-limiting examples.

EXAMPLE 1

Isolation of Plasmid pTN1060

*S. lactis* N1, cured of pME0030, was described previously as a variant of ME2 which efficiently adsorbed phage 18. Sanders, M. E. and T. R. Klaenhammer, *Appl. Environ. Microbiol.* 47, 979 (1984). The plasmid profiles of *S. lactis* N1, ME2, and *S. lactis* T-EK1 (Klaenhammer and Sanozky, supra) reveal that pME0030 was the only detectable difference in plasmid composition between strains N1 and ME2.

Conjugation procedures were carried out with *S. lacti* ME2 and N1 as donors, and with the plasmid-cured *S. lactis* LM0230 as recipients, on the surface of milk-glucose agar plates as described by McKay, L. L. et al., *Appl. Environ. Microbiol.* 40, 84 (1980). Lactose-indicator agar containing the appropriate concentrations of streptomycin (Sm) or erythromycin (Em) was used for selection and purification of Lac+ transconjugants. All procedures included donor-only and recipient-only controls. Lac+ transconjugants were verified by phenotype, phage-sensitivity, and plasmid analysis. Klaenhammer and Sanozky, supra.

Comparison of conjugative ability between *S. lactis* ME2 and N1, as shown in the above conjugation procedures, revealed frequencies for conjugal transfer of Lac+ from donor to recipient of $3.2 \times 10^{-3}$ for ME2 and $6.0 \times 10^{-7}$ for N1. When used as a donor, the pME0030-cured derivative N1 thus showed a four-log reduction in the frequency of conjugal transfer of Lac+. These data suggested that loss of pME0030 significantly retarded, but did not completely eliminate, the conjugal transfer ability of ME2.

Examination of the plasmid profiles of S. lactis N1 exconjugants revealed a variety of plasmids that were not observed following conjugation of Lac+ from S. lactis ME2 to LM0230. None of the N1 transconjugants exhibited the small plaque phenotype (Hsp+) when challenged with phage c2, suggesting that pME0030 was important for transfer of Hsp+ localized to the 30 Md conjugative plasmid, pTR2030. pME0030 and pTR2030 both approximate 30 MD in size and share substantial homology when examined by DNA-DNA hybridization experiments using pTR2030 probes. The plaquing efficiency of c2 phage was examined over TN1-Lac+ transconjugants. The majority of N1 exconjugants showed no significant alteration in the efficiency of plaquing (EOP's ranged from 1.0 to 0.12). However, strains TN1-9, TN1-20, TN1-24, and TN1-27 restricted c2 phage at EOP's of $2.4 \times 10^{-2}$, $3.1 \times 10^{-3}$, $4.9 \times 10^{-2}$, and $2.1 \times 10^{-2}$, respectively.

Each of the N1 transconjugants was further examined for the ability to act as a conjugal donor in subsequent matings with S. lactis LM2302. Frequencies for Lac+ transfer were highly variable, and ranged from $2 \times 10^{-6}$ to 6 Lac+ $Sm^r$ $Em^r$ recombinants per donor cell (Table 1). One of the donors, TN1-27, was a non-clumping culture, but mobilized Lac+ at extremely high frequency in agar surface matings.

TABLE 1

| Conjugal Ability of S. lactis N1 Lac+ Exconjugants. | |
|---|---|
| Lac+ Donor[a] | Lac+ $Sm^r$ $Em^r$ transconjugants/donor[b] |
| TN1-1 | $1.5 \times 10^{-5}$ |
| TN1-4 | $2.0 \times 10^{-6}$ |
| TN1-9 | $2.0 \times 10^{-5}$ |
| TN1-10 | $<6.1 \times 10^{-8}$ |
| TN1-11 | $1.1 \times 10^{-1}$ |
| TN1-17 | $<3.8 \times 10^{-8}$ |
| TN1-18 | $1.8 \times 10^{-1}$ |
| TN1-19 | $2.3 \times 10^{-5}$ |
| TN1-20 | $5.6 \times 10^{-1}$ |
| TN1-21 | $<4.5 \times 10^{-8}$ |
| TN1-24 | $1.5 \times 10^{-1}$ |
| TN1-27 | 6 |
| TN1-32 | 1.5 |

[a]Lac+ donors were isolated from matings between S. lactis N1 and S. lactis LM0230.
[b]Recipient was S. lactis LM2302 (Lac- $Sm^r$ $Em^r$).

TN1-27 carried a single 60 Md plasmid that, in curing experiments, was correlated with Lac+ and resistance to nisin ($Nis^r$). This plasmid was designated pTN1060.

EXAMPLE 2

Preparation of S. Lactis TN127-SS S. lactis TN1-27SS was isolated, as described by Sing and Klaenhammer, Appl. Environ. Microbiol. 51, 1264 (1986), as a Lac+ $Sm^s$ transconjugant from matings between TN127 (Lac+ $Sm^r$) and a Lac- $Sm^s$ plasmid-cured derivative of S. lactis C2, designated C145 (McKay, L. L., et al., Appl. Environ. Microbiol. 32, 45 (1976)). S. lactis TN127-SS containing pTN1060 was deposited on Nov. 24, 1986 under the Budapest Treaty at the American Type Culture Collection, and has been assigned number 67273. TN1-27-SS (Lac+ $Sm^s$) was used as a conjugal donor of pTN1060 to Lac- $Sm^r$ recipients in subsequent experiments.

EXAMPLE 3

Characterization and Mapping of pTN1060

The Lac+ $Nis^r$ plasmid from S. lactis ME2, pTR1040, exhibits no conjugal ability and relies on pTR2030 for mobilization (Klaenhammer and Sanozky, supra). pTN1060 also encoded Lac+ $Nis^r$, but was further capable of self-mobilization. These data suggested that pTN1060 was a derivative of pTR1040 where Tra+ determinants were acquired during conjugal events which mobilized Lac+ from S. lactis N1.

In the following procedures, large scale plasmid isolations were obtained in accordance with known techniques. Anderson, D. G. and McKay, L. L., Appl. Environ. Microbiol. 46, 549 (1983); Steenson, L. R. and T. R. Klaenhammer, Appl. Environ. Microbiol. 50, 851 (1985). Plasmid DNA preparations were purified once through cesium-chloride ethidium bromide (CsCl-EB) density gradients and examined by agarose gel electrophoresis. Steenson and Klaenhammer, supra. Hind III (BRL, Inc., Gaithersburg, Md.) digestions of pTN1060, pTR1040 and PTR2030 were conducted as described by Maniatis, et al., supra, and fragments separated on 0.8% agarose gels.

In a comparison of plasmids and Hind III digests of pTN1060 (60 Md, Lac+, $Nis^r$, Tra+), pTR1040 (40 Md, Lac+, $Nis^r$, Tra-), and pTR2030 (30 Md, Hsp+, Tra+), the majority of Hind III restriction fragments generated from pTR1040 were detected in digests of pTN1060. pTN1060 digestions showed additional Hind III fragments which were not detected in pTR1040.

The similarities and differences between pTR1040 and pTN1060 were confirmed using DNA probes and by restriction mapping. Restriction enzyme digestions for comparative mapping of pTN1060 and pTR1040 were performed using BglI, BamHI, PvuI, PstI, SmaI, and SalI enzymes (IBI, Inc., New Haven, Conn.) on DNA samples purified twice through CsCl-EB gradients. Separation of fragments was on horizontal 0.4% agarose gels where lambda DNA high molecular weight markers (BRL, Inc., Cat No. 5618SA) served as the molecular weight reference. Southern transfer of plasmid DNA from agarose gels to nitrocellulose filters (Schleicher & Schuell Co., Keene, N.H.) and hybridization reactions were as described previously (Southern, E. M., J. Mol. Biol. 98, 503 (1975); Jarvis, A. W., Appl. Environ. Microbiol. 47, 343 (1984)). 32p-labeled probes of pTN1060 and pTR1040 were prepared by nicked translation (Amersham Corp., Arlington Heights, Ill.) according to the manufacturers' specifications. pTN1060 and pTR1040 were isolated from large scale DNA preparations of S. lactis TN127 and S. lactis T-

RS3, respectively, and were purified once through CsCl-EB gradients prior to use in nicked translation reactions. $^{32}$P-labeled probes of pTR1040 hybridized to all Hind III fragments of pTN1060 except those apparently representing the 20 Md insertion. It was of further interest that pTN1060 probes did not hybridize to sequences in the conjugal plasmid pTR2030 over that observed with $^{32}$P-pTR1040 probes. This suggested that the Tra+ determinants associated with pTN1060 were different from pTR2030. Restriction maps of pTN1040 and pTN1060 were constructed and the position of the 20 Md insertion identified in the map of pTR1040 (See Figure). Physical analysis and genetic properties of the two plasmids provided conclusive evidence that conjugal transfer of Lac+ from *S. lactis* N1 resulted in a recombinational event between pTR1040 and a 20 Md DNA sequence encoding Tra+ to generate the conjugative plasmid pTN1060.

EXAMPLE 4

Demonstration of R/M+Activities Encoded by pTN1060

Taking advantage of the conjugal ability and genetic markers associated with pTN1060 (Lac+ Nis$^r$), the plasmid was introduced into *S. lactis* L2FA, *S. lactis* 25SpR, *S. cremoris* M43a, and *S. cremoris* KH-M5 by conducting agar surface matings with an *S. lactis* TN-127SS donor.

pTN1060 transconjugants were constructed within these host strains in order to evaluate the effects of this plasmid on the plaquing efficiencies of small isometric-, large isometric-, and prolate-headed phages. Table 2 shows that plaquing efficiencies for all three phage species were restricted on pTN1060 transconjugants, but the level of restriction varied. Prolate phages c2 and 923 were least subject to restriction by pTN1060 transconjugants (EOP=10$^{3\ 1\ 2}$ in *S. cremoris* T-KH-M5 and *S. lactis* T-S8), plaque formation of the large isometric phage 949 was completely inhibited by *S. lactis* T-L2-6. For three small isometric phages (m12r.M12, kh and 31) attacking *S. cremoris* M43a, *S. cremoris* KH-M5 and *S. lactis* L2FA, respectively, plaquing efficiencies on pTN1060 transconjugants were reduced to levels between $10^{-4}$ and $10^{-5}$. The data demonstrated that phage restriction imposed by pTN1060 affects all three phage species attacking either *S. lactis* or *S. cremoris* hosts.

TABLE 2 pTN1060 Restricts Plaquing Efficiencies of Small Isometric, Large Isometric, and Prolate Phages Propagating on *S. lactis* and *S. cremoris*.

| Host | Description | % ads | PFU/ml | EOP |
|---|---|---|---|---|
| | | | phage 31 (SI)$^a$ | |
| L2FA | Lac−, parent | 86.8 | 64.4 × 10$^9$ | 1 |
| T-L2-6 | Lac+, pTN1060 | 99.4 | 2.9 × 10$^5$ | 4.5 × 10$^{-5}$ |
| | | | phage 949 (LI)$^a$ | |
| L2FA | Lac−, parent | 98.7 | 4.0 × 10$^9$ | 1 |
| T-L2-6 | Lac+, pTN1060 | 99.6 | <10 | <4.0 × 10$^{-8}$ |
| | | | phage kh (SI)$^a$ | |
| KH-M5 | Lac−, parent | ND | 6.0 × 10$^8$ | 1 |
| T-KH-M5 | Lac+, pTN1060 | ND | 4.5 × 10$^5$ | 7.5 × 10$^{-4}$ |
| | | | phage 923 (P)$^a$ | |
| KH-M5 | Lac−, parent | ND | 1.0 × 10$^9$ | 1 |
| T-KH-M5 | Lac+, pTN1060 | ND | 4.6 × 10$^7$ | 4.6 × 10$^{-2}$ |
| | | | phage c2 (P)$^a$ | |
| 25 SpR | Lac−, parent | 69 | 9.3 × 10$^8$ | 1 |

TABLE 2-continued pTN1060 Restricts Plaquing Efficiencies of Small Isometric, Large Isometric, and Prolate Phages Propagating on *S. lactis* and *S. cremoris*.

| Host | Description | % ads | PFU/ml | EOP |
|---|---|---|---|---|
| T-S8 | Lac+, pTN1060 | 57 | 1.1 × 10$^7$ | 1.2 × 10$^{-2}$ |
| | | | phage m12r.M12 (SI)$^a$ | |
| M43a | Lac−, parent | ND | 1.2 × 10$^{10}$ | 1 |
| TH6-M43a | Lac+, pTN1060 | ND | 5.5 × 10$^6$ | 6.4 × 10$^{-4}$ |

$^a$SI = small isometric phage
LI = large isometric phage
p = prolate phage
$^b$not determined affects all three phage species attacking either *S. lactis* or *S. cremoris* hosts. Plaquing efficiencies wre reduced without effects on phage adsorption (Table 2).

Plaquing efficiencies of modified phages c2.T-S8 and m12r.TH6-M43a were no longer restricted on pTN1060 transconjugants of *S. lactis* T-S8 and *S. cremoris* H6-M43a, respectively. These reactions implicated operation of both restriction and modification activities (R/M+) in pTN1060 transconjugants. Determinants for R/M+ activities were localized to pTN1060 noting: (i) acquisition of the 60 Md plasmid in all R/M+Lac+ and Nis$^r$ transconjugants; and (ii) concurrent loss of R/M+, Lac+ and Nis$^r$ upon curing of pTN1060 from the transconjugants.

EXAMPLE 5

Genetic Construction of Multiple Levels of R/M+

Two isogeneic derivatives, M43a and CN9S, of *S. cremoris* M12R (Steenson and Klaenhammer, supra), were used as recipients in conjugation experiments designed to construct multiple levels of R/M+ activity by combining pTN1060 with a second plasmid linked to R/M+ (Table 3). *S. cremoris* CN9S (Lac−, R/M+, Sm$^r$) restricted phage m12r.M12 at an EOP of 10$^{-3}$ (Table 3) and harbored a 20 Md plasmid, pLR1020, correlated previously with R/$^M$+ activities.

Strain TH6-M43a was deficient in pLR1020, but exhibited phage restriction at an EOP of 6.4 ×10$^{-4}$ when pTN1060 was present. Matings were then conducted between TN127-SS (Lac+, pTN1060) and CN9S (Lac−, pLR1020) to combine pTN1060 and pLR1020 in the CN9S background. Two Lac+ transconjugants (T-CN-7 and T-CN-8) that harbored both plasmids were isolated and examined for additive levels of phage restriction. The presence of both pTN1060 and pLR1020 yielded higher orders of restriction than were observed with either plasmid alone (Table 3).

TABLE 3

Use of pTN1060 for Construction of Multiple Levels of Phage Restriction in *S. cremoris*.

| | | phage m12r.M12 | |
|---|---|---|---|
| *S. cremoris* | Description | PFU/ml | EOP |
| M12 | phage propagating host | 5.0 × 10$^9$ | 1 |
| H6-M43a | Lac+, R/M+, + pTN1060 | 5.5 × 10$^6$ | 6.4 × 10$^{-4}$ |
| CN9S | Lac−, R/M+, + pLR1020 | 5.1 × 10$^6$ | 1.0 × 10$^{-3}$ |
| T-CN-8$^a$ | Lac+, R/M+, + pLR1020 +pTN1060 | 1.9 × 10$^5$ | 3.8 × 10$^{-5}$ |
| T-CN-7$^a$ | Lac+R/M+, + pLR1020 +pTN1060 | 3.2 × 10$^2$ | 6.4 × 10$^{-8}$ |

$^a$Lac+ transconjugants generated from matings between *S. lactis* TN1-27SS (Lac+, Sm$^r$, R/M+ containing pTN1060) and *S. cremoris* CN9S (Lac−, Sm$^r$, R/M+ containing pLR1020).

One of the Lac+ transconjugants (T-CN-7) restricted m12r.-M12 phage at an EOP of $10^{-8}$. This value was slightly higher than the levels of phage restriction expected for combined activity of pTN1060 ($10^{-4}$) and pLR1020 ($10^{-3}$) encoded systems. In contrast, T-CN-8 exhibited a 100-fold higher level of phage restriction over CN9S, but was less than observed with T-CN-7. The only detectable difference between T-CN-7 and T-CN-8 was absence of two smaller plasmids (pLR4005, 5.3 Md and pLR7002, 2.6 Md) in the T-CN-8 transconjugant. Upon curing of pTN1060 from T-CN-7 and T-CN-8, Lac- derivatives from both strains retained all their respective resident plasmids, including pLR1020, and resumed EOP levels of CN9S. Therefore, if pLS4005 or pLS7002 enhanced the level of restriction exhibited by T-CN-7, effects on the plaquing efficiency of phage m12r.M12 occurred in the presence of both pTN1060 and pLR1020, but not pLR1020 alone. Any effects of the smaller plasmids on only pTN1060 R/M+activities could not be clearly evaluated because the transconjugant strain TH6-M43a (+pTN1060, -pLR1020) was also deficient in these two small plasmids. These data illustrate the desirability of preparing microorganisms which further contain a second, different, plasmid carrying a genetic determinant for bacteriophage restriction and modification activity, and starter cultures containing such microorganisms.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

That which is claimed is:

1. The plasmid pTN1030 (ATCC Accession Number 67273) characterized by a molecular weight of 60.0±3.0 megadaltons, having the restriction endonuclease cleavage map as shown in the Figure, and capable of expressing restriction and modification activity, conjugal transfer activity, and lactose fermentation activity in a suitable host.

2. A plasmid which comprises a derivative of the plasmid pTN 1060, ATCC Accession Number 67273, characterized by a molecular weight of 60.0±3.0 megadaltons, having the restriction endonuclease cleavage map as shown in the Figure, wherein said derivative retains the capability of plasmid pTN1060 of expressing restriction and modification activity in a suitable host.

3. The plasmid of claim 2 wherein said derivative further retains the capability of plasmid pTN1060 of expressing conjugal transfer activity in a suitable host.

4. The plasmid of claim 3 wherein said derivative further retains the capability of plasmid pTN1060 of expressing lactose fermentation activity in a suitable host.

5. A microorganism containing the plasmid of claim 1, said microorganism selected from the group consisting of *Streptococcus lactis, S. lactis* subsp. *diacetylactis,* and *S. cremoris.*

6. A microorganism containing the plasmid of claim 2, said microorganism selected from the group consisting of *Streptococcus lactis, S. lactis* subsp. *diacetylactis,* and *S. cremoris.*

7. A microorganism containing the plasmid of claim 3, said microorganism selected from the group consisting of *Streptococcus lactis, S. lactis* subsp. *diacetylactis,* and *S. cremoris.*

8. A microorganism containing the plasmid of claim 4, said microorganism selected from the group consisting of *Streptococcus lactis, S. lactis* subsp. *diacetylactis,* and *S. cremoris.*

9. A starter culture capable of fermenting milk which comprises the microorganism of claim 5.

10. A starter culture capable of fermenting milk which comprises the microorganism of claim 6.

11. A starter culture capable of fermenting milk which comprises the microorganism of claim 7.

12. A starter culture capable of fermenting milk which comprises the microorganism of claim 8.

* * * * *

UNITED STATES PATENT AND TRADEMARK OFFICE
CERTIFICATE OF CORRECTION

PATENT NO. : 4,883,756

DATED : November 28, 1989

INVENTOR(S) : Todd R. Klaenhammer and Rosemary B. Sanozky-Dawes

It is certified that error appears in the above-identified patent and that said Letters Patent is hereby corrected as shown below:

Claim 1, Column 11, line 38, "pTN1030" should read --pTN1060--.

Column 2, line 45, "Appl" should read --Appl.--.

Column 5, line 3, after "$Lac^+$, $Nis^r$" insert a colon.

Column 6, line 11, "S. lacti" should read --S. lactis--.

Column 9, line 38, "EOP = $10^{31}$ $^2$" should read --EOP = $10^{-2}$--.

Column 9, line 39, insert "whereas" before the word plaque.

Column 10, lines 15 and 16, "affects all three phage species attacking either S. lactis or S. cremoris hosts" has been duplicated and should be deleted.

UNITED STATES PATENT AND TRADEMARK OFFICE
CERTIFICATE OF CORRECTION

PATENT NO. : 4,883,756

DATED : November 28, 1989

INVENTOR(S) : Todd R. Klaenhammer and Rosemary B. Sanozky-Dawes

It is certified that error appears in the above-identified patent and that said Letters Patent is hereby corrected as shown below:

Column 10, line 16, "wre" should read --were--.

Column 10, line 41, "R/$M+$" should read --R/$M^+$--.

Signed and Sealed this

Sixth Day of November, 1990

Attest:

HARRY F. MANBECK, JR.

Attesting Officer

Commissioner of Patents and Trademarks